(12) United States Patent
Buehring et al.

(10) Patent No.: US 7,696,385 B2
(45) Date of Patent: Apr. 13, 2010

(54) POLYETHERAMINE PRODUCTION METHOD

(75) Inventors: Dirk Buehring, Burghausen (DE); Andreas Gallas, Erlbach (DE); Martin Glos, Essen (DE); Klaus Raab, Burgkirchen (DE); Franz-Xaver Scherl, Burgkirchen (DE); Olaf Wachsen, Garching (DE)

(73) Assignee: Clariant Produkte (Deutschland) GmbH, Frankfurt (DE)

( * ) Notice: Subject to any disclaimer, the term of this patent is extended or adjusted under 35 U.S.C. 154(b) by 0 days.

(21) Appl. No.: 11/922,856

(22) PCT Filed: Jun. 10, 2006

(86) PCT No.: PCT/EP2006/005577
§ 371 (c)(1),
(2), (4) Date: Jan. 9, 2009

(87) PCT Pub. No.: WO2007/000236
PCT Pub. Date: Jan. 4, 2007

(65) Prior Publication Data
US 2009/0177013 A1 Jul. 9, 2009

(30) Foreign Application Priority Data
Jun. 28, 2005 (DE) .................. 10 2005 029 932

(51) Int. Cl.
C07C 209/16 (2006.01)
(52) U.S. Cl. .................. 564/474; 564/479; 564/480
(58) Field of Classification Search .................. None
See application file for complete search history.

(56) References Cited

U.S. PATENT DOCUMENTS

| 4,014,933 | A | * | 3/1977 | Boettger et al. ............. 564/447 |
| 4,618,717 | A | | 10/1986 | Renken et al. |
| 4,766,245 | A | | 8/1988 | Larkin et al. |
| 4,960,942 | A | * | 10/1990 | Gerkin et al. ............. 564/479 |
| 5,003,107 | A | | 3/1991 | Zimmerman et al. |
| 5,331,101 | A | * | 7/1994 | Habermann ............. 564/480 |
| 5,352,835 | A | | 10/1994 | Dai et al. |
| 5,530,127 | A | | 6/1996 | Reif et al. |
| 6,191,310 | B1 | * | 2/2001 | Knifton et al. ............. 564/479 |
| 6,376,713 | B1 | * | 4/2002 | Baiker et al. ............. 564/479 |
| 6,462,236 | B2 | * | 10/2002 | Liang et al. ............. 564/336 |
| 2003/0139289 | A1 | | 7/2003 | Renken et al. |
| 2005/0107637 | A1 | | 5/2005 | Gerlach et al. |

FOREIGN PATENT DOCUMENTS

| DE | 1 570 542 | 2/1965 |
| DE | 1 643 426 | 12/1967 |
| DE | 1 953 263 | 10/1969 |
| DE | 36 08 716 | 12/1986 |
| DE | 44 28 004 | 2/1996 |
| DE | 102 11 101 | 9/2003 |
| EP | 0 343 486 | 11/1989 |
| EP | 0 436 235 | 7/1991 |
| GB | 1185239 | 3/1970 |
| GB | 1 319 495 | 6/1973 |
| GB | 2 175 910 | 12/1986 |

* cited by examiner

Primary Examiner—Brian J Davis
(74) Attorney, Agent, or Firm—Tod A. Waldrop

(57) ABSTRACT

The invention relates to a method for producing amines of formula (1),

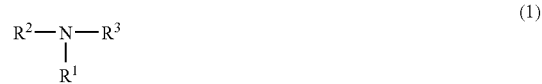

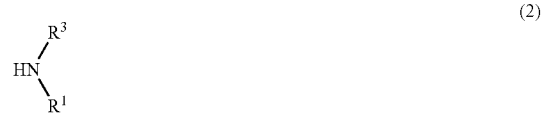

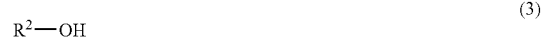

wherein $R^3$ is an organic group containing from 2 to 600 alkoxy groups and $R^1$ and $R^3$ groups are similar or different and represent a hydrogen atom or an organic group containing from 1 to 400 carbon atoms. The inventive method consists in bringing a compound of formula (2) into contact a compound of formula (3) in the presence of hydrogen with a metal-containing catalyst, wherein the metal content in cobalt is equal to or greater than 80% by weight.

8 Claims, No Drawings

POLYETHERAMINE PRODUCTION METHOD

This application is a 371 of PCT/EP2006/005577 Jun. 10, 2006.

The present invention relates to a process for preparing polyetheramines using cobalt catalysts.

Polyetheramines contain at least one polyalkylene glycol group, which crucially influences their properties. A high proportion of polyethylene glycol units gives rise to water-soluble polyetheramines, and a high proportion of polypropylene glycol units to water-insoluble polyetheramines. Moreover, the change in the molar masses of the polyalkylene glycols allows melting point and viscosity of the polyetheramines to be influenced. By virtue of the selection of suitable starter alcohols for the alkoxylation, it is possible to achieve surfactant properties. Moreover, it is possible with polyhydric alcohols to form branched polyetheramines which then lead, after aminolysis, to polyfunctional amines. This gives rise to various means of influencing the properties of a polyetheramine based thereon in a controlled manner by the selection of suitable polyalkylene glycols.

The prior art discloses various processes for preparing polyetheramines.

DE-A-16 43 426 describes a process for preparing polyoxyalkyleneamines proceeding from the corresponding alcohols using a nickel-copper-chromium catalyst which contains 60-85 mol % of nickel, 14-37 mol % of copper and 1-5 mol % of chromium.

U.S. Pat. No. 4,618,717 describes a process for preparing primary amines proceeding from oxyethylene glycol monoalkyl ethers using a catalyst which contains 50-90% by weight of nickel, 10-15% by weight of copper and 0.5-5% by weight of the elements chromium, iron, titanium, thorium, zirconium, manganese, magnesium or zinc.

U.S. Pat. No. 5,352,835 describes a supported catalyst for aminolysis, which is used for the conversion of polyoxyalkylene glycols to the corresponding amines. In this case, the catalyst consists of 15-30% by weight of nickel, 3-20% by weight of copper, 0.5-1% by weight of molybdenum and at least 50% by weight of γ-aluminum oxide, which serves as the support material.

U.S. Pat. No. 4,766,245 describes a process for preparing polyoxyalkylenepolyamines proceeding from the corresponding alcohols using a Raney nickel/aluminum catalyst which consists of nickel to an extent of 60-75% and of aluminum to an extent of 40-25%.

DE-A-36 08 716 describes a process for preparing polyoxyalkylenepolyamines proceeding from the corresponding alcohols using a Raney nickel or Raney nickel/aluminum catalyst which additionally also contains 0.2-5% molybdenum.

U.S. Pat. No. 5,003,107 describes a process for reductive amination of polyoxytretramethylene glycols using a catalyst which contains 70-75% by weight of nickel, 20-25% by weight of copper, 0.5-5% by weight of chromium and 1-5% by weight of molybdenum.

DE-A44 28 004 describes a process for preparing amines proceeding from alcohols, in which the catalyst contains 20-85% Zr, 1-30% Cu, 30-70% Ni, 0.1-5% Mo, 0-10% aluminum and/or manganese, in each case calculated as the oxide.

US-A-2003/0139289 describes an improved process for preparing amines proceeding from alcohols, aldehydes or ketones by means of a catalyst which, as well as nickel, copper and chromium, also comprises tin.

DE-A-19 53 263 describes a process for preparing amines proceeding from alcohols by means of a catalyst. The metal content of the catalyst consists of Co and Ni to an extent of 70 to 95% and of copper to an extent of 5 to 30%. In this catalyst, the weight ratio of Co to Ni ranges from 4:1 to 1:4.

DE-A-102 11 101 describes a process for preparing amines proceeding from alcohols or aldehydes, in which the catalyst contains 22-40% Zr, 1-30% Cu, 15-50% Ni, 15-50% Co, calculated in each case as the oxides.

DE-A-15 70 542 discloses a process for preparing polyetheramines, characterized in that polyethers of the formula I or II

HO—R—(OR)$_n$-OH       (I)

Z[(OR)$_n$—OH]$_m$       (II)

in which R is an aliphatic radical having 2-4 carbon atoms, Z is a divalent to hexavalent aliphatic, araliphatic, aromatic or alicyclic radical which may be interrupted once or more than once by ether or amino groups, carbonamide, urethane or urea groups, n is integers from 1 to 50 and m=2 to 6 according to the valency of Z, in the presence of water and hydrogen over a hydrogenation-dehydrogenation catalyst consisting mainly of an element of the 8th transition group is reacted with ammonia at 200-280° C., preferably 220-250° C., under pressure.

It has now been found that, surprisingly, polyetheramines or polyoxyalkyleneamines can be prepared from the corresponding alcohols and ammonia or amines (in the presence of hydrogen) by using a catalyst whose metal content consists of cobalt to an extent of at least 80% by weight.

It is possible here to use either support catalysts which, apart from the catalytically active metal content, also comprise support material, and metal catalysts without additional support material, for example the so-called "Raney types".

The process is suitable both for continuous and batchwise preparation of polyetheramines.

The invention thus provides a process for preparing amines of the formula I

in which R$^2$ is an organic radical which comprises between 2 and 600 alkoxy groups, and R$^1$ and R$^3$ are the same or different and are each hydrogen or an organic radical having from 1 to 400 carbon atoms, by combining a compound of the formula 2

with a compound of the formula 3

R$^2$—OH in the presence of hydrogen with a catalyst which is metallic and whose metal content consists of cobalt to an extent of at least 80% by weight.

The catalyst used for the process according to the invention contains preferably 85, more particularly 90, especially 95% by weight of cobalt, based on the total metal content of the catalyst. The catalyst may, as well as cobalt, also comprise nickel, copper, chromium, iron, titanium, thorium, zirconium, manganese, magnesium, molybdenum aluminum, zinc and/or tin.

The catalyst may be a supported catalyst or an unsupported catalyst.

When the catalyst is unsupported, it is preferably a Raney-type catalyst.

When the catalyst is supported, the support particles of the catalyst may have any geometric shape, for example the shape of spheres, tablets or cylinders in a regular or irregular version. The dimensions of the support particles are generally between 1 and 8 mm. Preference is given to the spherical form, for example spheres having a diameter of from 4 to 8 mm. The support particles are generally referred to as pellets.

Suitable supports are the known inert support materials such as silica, aluminum oxide, aluminum silicates, silicates, titanium oxide, zirconium oxide, titanates, silicon carbide and carbon. Particularly suitable supports of this type are those having a specific surface area of from 50 to 300 m²/g (measured by the BET method) and a mean pore radius of from 50 to 2000 Å (measured by mercury porosimetry), in particular silica ($SiO_2$) and $SiO_2$—$Al_2O_3$ mixtures.

In the case of supported catalysts, the metal contents may be between 1 and 99%, preferably in the range from 5 to 70%.

$R^2$ contains from 2 to 600 alkoxy groups. In the present context, alkoxy groups are understood to mean a unit of the formula -(AO)— in which A is a $C_2$- to C4-alkylene group. From 2 to 600 alkoxy groups thus mean a structural unit of the formula -(AO)$_n$— where n=from 2 to 600.

In the alkoxy chain represented by (A-O)$_n$, A is preferably an ethylene or propylene radical, especially an ethylene radical. The total number of alkoxy units is preferably between 5 and 300, especially between 8 and 200. The alkoxy chain may be a block polymer chain which has alternating blocks of different alkoxy units, preferably ethoxy and propoxy units. It may also be a chain having a random sequence of the alkoxy units, or a homopolymer.

In a preferred embodiment, -(A-O)$_n$— is an alkoxy chain of the formula 4

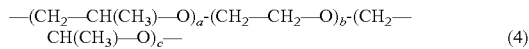
(4)

in which
a is from 0 to 300, preferably from 0 to 80,
b is from 3 to 300, preferably from 3 to 200,
c is from 0 to 300, preferably from 0 to 80.

$R^1$ and $R^3$ are the same or different and are each hydrogen or an organic radical having from 1 to 400 carbon atoms. $R^1$ and $R^3$ may, as well as carbon and hydrogen, also contain heteroatoms such as oxygen, nitrogen, phosphorus or sulfur.

In a preferred embodiment, $R^1$ and $R^3$ are each hydrogen, an alkyl radical having from 1 to 50 carbon atoms, an alkylene radical having from 2 to 50 carbon atoms, an aryl radical having from 6 to 50 carbon atoms or an alkylaryl radical having from 7 to 50 carbon atoms.

In a further preferred embodiment, $R^1$ and $R^3$ are each as defined for $R^2$.

In a further preferred embodiment, $R^1$ and $R^3$ each contain amino groups. $R^1$ and $R^3$ then correspond to the formula 5

(5)

in which $R^4$ is a divalent hydrocarbon group having from 1 to 50 carbon atoms and $R^5$ and $R^6$ may each be hydrogen or a monovalent hydrocarbon group having from 1 to 50 carbon atoms, where each of $R^4$, $R^5$ and $R^6$ may comprise from 1 to 200 alkoxy groups and heteroatoms such as oxygen, nitrogen, phosphorus or sulfur (basically in the same way as $R^3$), and m is from 1 to 10.

When $R^2$ is alkoxylated methanol, the product of the process according to the invention may, for example, have the following structures:

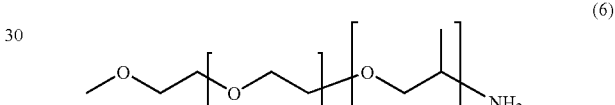
(6)

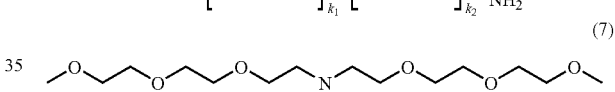
(7)

In the case of an alkoxylated alkyl alcohol, the following structure arises:

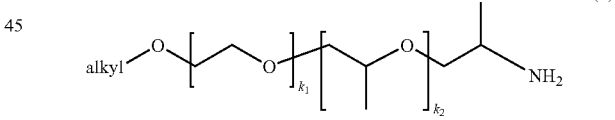
(8)

In the case of polyalkylene glycols (diols), the following structures arise:

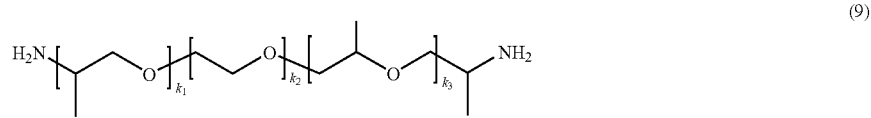
(9)

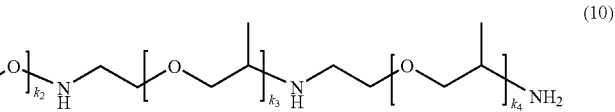
(10)

in which $k_1$, $k_2$, $k_3$ and $k_4$ are each integers which add up to 600.

In a further preferred embodiment, the amine of the formula (1) is a polyamine of the formula 11

$$R^7(NR^9R^8)_n \quad (11)$$

in which $R^7$ is an n-valent organic radical which has from 2 to 400 carbon atoms and may also contain heteroatoms such as oxygen, nitrogen, phosphorus or sulfur, $R^8$ and $R^9$ are each a radical as for $R^3$, and n is an integer from 2 to 20.

When $R^7$ is alkoxylated glycerol, the product of the process according to the invention may, for example, have the following structure:

glycol units, butanediol polyalkylene glycol diamine, resorcinol polyalkylene glycol diamine, trifunctional amines, for example glycerol polyalkylene glycol triamine with random or blockwise distribution of the ethylene glycol and propylene glycol units, bis(triethylene glycol amine) amine, bis(polyalkylene glycol amine) amine, tetrafunctional amines, for example pentaerythritol polyalkylene glycol tetraamine with random or blockwise distribution of the ethylene glycol and propylene glycol units, N,N'-bis(polypropylene glycol amine) polyalkylene glycol diamine.

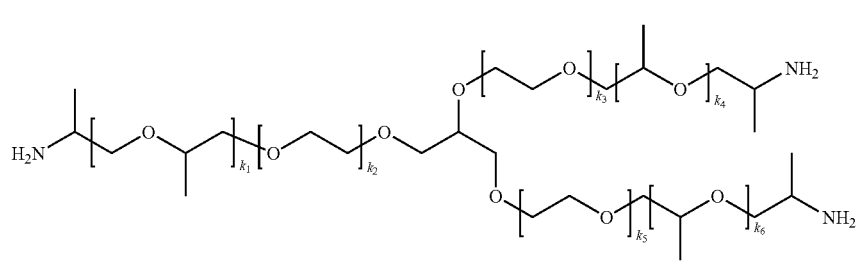

(12)

in which the indices $k_n$ are integers which add up to 600.

When $R^7$ is alkoxylated octylamine, the product of the process according to the invention may, for example, have the following structure:

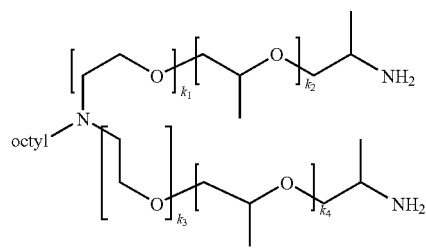

(13)

in which the indices $k_n$ are integers which add up to 600.

Inventive polyetheramines are mono- or polyfunctional amines which may be branched, unbranched or cyclic, saturated or unsaturated. Such amines are, for example, monofunctional amines, for example alkyl polyalkylene glycol amines, for example methyl triethylene glycol amine, bis(methyl triethylene glycol) amine, butyl triethylene glycol amine, lauryl polypropylene glycol amine, methyl tripropylene glycol amine, phenol polypropylene glycol amine, isotridecyl polypropylene glycol amine, bis(methyl tripropylene glycol) amine, N-methyl methyl polypropylene glycol amine, methyl polypropylene glycol amine, bis(methyl polypropylene glycol) amine, tris(methyl diglycol) amine, methyl polyalkylene glycol amine with random or blockwise distribution of the ethylene glycol and propylene glycol units, difunctional amines, for example triethylene glycol diamine, tripropylene glycol diamine, polyethylene glycol diamine, polypropylene glycol diamine, polyalkylene glycol diamine with random or blockwise distribution of ethylene glycol and propylene The aminating agents used in the reductive amination of the polyether alcohols to give the amines by the process according to the invention may be either ammonia or primary or secondary, aliphatic or cycloaliphatic or aromatic amines.

In the case of use of ammonia as the aminating agent, a primary amine is initially formed. Under appropriate reaction conditions (pressure, temperature, reaction time), this can be isolated as the product, or the reaction is continued such that the primary amine formed reacts further with further alcohol to give the corresponding secondary or else tertiary amine.

In addition to ammonia, the following amines, for example, can be used as aminating agents: methylamine, dimethylamine, ethylamine, diethylamine, n-propylamine, di-n-propylamine, isopropylamine, diisopropylamine, hexylamine, cyclohexylamine, aniline, toluidine, piperidine, morpholine.

The aminating agent may, based on the hydroxyl group to be aminated, be used in stoichiometric, substoichiometric or superstoichiometric amounts. The amount of hydrogen to be used may likewise be varied within a wide range, from substoichiometric to superstoichiometric.

The process according to the invention is performed preferably at temperatures of from 50 to 250° C., especially at temperatures of from 140° C. to 200° C.

The process according to the invention is performed preferably at pressures of from 1 bar to 300 bar, especially at pressures of from 30 bar to 200 bar.

The amount of catalyst to be used is preferably in the range from 0.5 to greater than 90% by weight, more particularly from 1 to 80% by weight, especially from 2 to 70% by weight, based on the alcohol used. Amounts above 70% by weight are used especially in continuous processes.

The amination can be performed continuously or batchwise. In both processes, the gaseous or in some cases even supercritical reaction components (aminating agent, hydrogen and possibly inert gases) can be circulated.

The water which forms during the reaction can either remain in the reaction mixture or else optionally be removed if the desired conversion otherwise suffers with regard to yield and/or selectivity.

The amination is preferably performed without solvent. However, it is also possible to use solvents.

The resulting reaction effluent is freed of excess aminating agent, hydrogen and optionally inert gases, and the amine is further purified appropriately according to the requirement. The reaction components removed may, possibly after appropriate workup, be sent back to the amination process.

EXAMPLES

Example 1

1.5 kg of methyl polyalkylene glycol with a mean molar mass of 2000 g/mol, 300 g of a supported catalyst whose metal content consisted of cobalt to an extent of more than 90% and 800 ml of ammonia (liquid) were metered into an agitated autoclave of capacity 4.5 l. Subsequently, 10 bar hydrogen were injected and the autoclave was closed. The mixture was heated to 190° C. while being agitated for 8 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 85% to the corresponding amine to be determined.

Example 2

1 kg of methyl polyalkylene glycol with a mean molar mass of 2000 g/mol, 200 g of a supported catalyst whose metal content consisted of cobalt to an extent of more than 90% and 540 ml of ammonia (liquid) were metered into a stirred autoclave of capacity 2 l. Subsequently, 30 bar hydrogen were injected and the autoclave was closed. The mixture was heated to 190° C. while being stirred for 7 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding amine to be determined.

Example 3

1 kg of methyl polyalkylene glycol with a mean molar mass of 2000 g/mol, 180 g of cobalt catalyst of the Raney type, and 540 ml of ammonia (liquid) were metered into a stirred autoclave of capacity 2 l. Subsequently, 10 bar hydrogen were injected and the autoclave was closed. The mixture was heated to 190° C. while being stirred for 6 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding amine to be determined.

Example 4

750 g of polyalkylene glycol consisting of ethylene glycol and propylene glycol units and having a mean molar mass of 600 g/mol, 150 g of a supported catalyst whose metal content consisted of cobalt to an extent of more than 90% and 800 ml of ammonia (liquid) were metered into a stirred autoclave of capacity 4.5 l. Subsequently, 10 bar hydrogen were injected and the autoclave was closed. The mixture was heated to 190° C. while being agitated for 6 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding amine to be determined.

Example 5

1 kg of polyalkylene glycol consisting of ethylene glycol and propylene glycol units and having a mean molar mass of 4000 g/mol, 200 g of a supported catalyst whose metal content consisted of cobalt to an extent of more than 80% and 540 ml of ammonia (liquid) were metered into a stirred autoclave of capacity 2 l. Subsequently, 10 bar hydrogen were injected and the autoclave was closed. The mixture was heated to 190° C. while being stirred for 5 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 95% to the corresponding amine to be determined.

Example 6

1.5 kg of methyl polyalkylene glycol with a mean molar mass of 2000 g/mol, 100 g of cobalt catalyst of the Raney type and 800 ml of ammonia (liquid) were metered into an agitated autoclave of capacity 4.5 l. Subsequently, 10 bar hydrogen were injected and the autoclave was closed. The mixture was heated to 190° C. while being agitated for 12 hours, a pressure of 180 bar being maintained by injecting further hydrogen. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 85% to the corresponding amine to be determined.

Example 7

1 kg of fatty alcohol oxypropylate with a mean molar mass of 310 g/mol, 200 g of a supported catalyst whose metal content consisted of cobalt to an extent of more than 90% and 540 ml of ammonia (liquid) were metered into a stirred autoclave of capacity 2 l. Subsequently, 5 bar hydrogen were injected and the autoclave was closed. The mixture was heated to 190° C. while being stirred for 8 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 80% to the primary amine to be determined. No content of sec- and tert-amines was detectable.

Example 8

1 kg of fatty alcohol oxypropylate with a mean molar mass of 310 g/mol, 50 g of a supported catalyst whose metal content consisted of cobalt to an extent of more than 95% and 540 ml of ammonia (liquid) were metered into a stirred autoclave of capacity 2 l. Subsequently, 5 bar hydrogen were injected and the autoclave was closed. The mixture was heated to 190° C. while being stirred for 24 hours. After cooling, the autoclave was slowly decompressed in order to remove the ammonia and the hydrogen. The remaining reaction mixture was freed of residual volatile constituents under reduced pressure and filtered. The determination of the amine number allowed a degree of conversion of 75% to the corresponding primary amine to be determined. The content of sec- and tert-amines was <1 mol %.

Example 9

A fixed bed reactor having a diameter of 5 cm and a length of 2.5 m was charged with tablets of a supported catalyst whose metal content consisted of cobalt to an extent of more than 90%, and the catalyst was activated under reductive conditions. Subsequently, 1 kg/h of fatty alcohol propoxylate having a mean molar mass of 310 g/mol, 2.5 kg/h of ammonia and 50 l/h of hydrogen were fed into the reactor at a temperature of 190° C. and a pressure of 100 bar. Once stable reaction conditions had been established in the reactor, samples of the product effluent were taken. The determination of the amine number allowed a conversion of greater than 98% to be determined.

Example 10

As described in Example 9, a fixed bed reactor was charged with catalyst and conditioned. Subsequently, 1 kg/h of fatty alcohol propoxylate having a mean molar mass of 310 g/mol, 2.5 kg/h of ammonia and 50 l/h of hydrogen were fed into the reactor at a temperature of 195° C. and a pressure of 190 bar. Once stable reaction conditions had been established in the reactor, samples of the product effluent were taken. The determination of the amine number allowed a conversion of greater than 95% to be determined.

Example 11

As described in Example 9, a fixed bed reactor was charged with catalyst and conditioned. Subsequently, 1 kg/h of methyl polyalkylene glycol having a mean molar mass of 2000 g/mol, 1.5 kg/h of ammonia and 100 l/h of hydrogen were fed into the reactor at a temperature of 195° C. and a pressure of 190 bar. Once stable reaction conditions had been established in the reactor, samples of the product effluent were taken. The determination of the amine number allowed a conversion of greater than 95% to be determined.

The invention claimed is:

1. A process for preparing an amine of the formula I

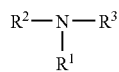
(1)

in which $R^2$ is an organic radical which comprises between 2 and 600 alkoxy groups, and $R^1$ and $R^3$ are the same or different and are each hydrogen or an organic radical having from 1 to 400 carbon atoms, by combining a compound of the formula 2

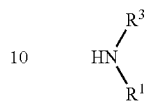
(2)

with a compound of the formula 3

in the presence of hydrogen with a catalyst which is metallic and whose metal content comprises cobalt to an extent of at least 95% by weight.

2. The process as claimed in claim 1, in which $R^1$ and $R^3$ are each selected from the group consisting of hydrogen, an alkyl radical having from 1 to 50 carbon atoms, an alkylene radical having from 2 to 50 carbon atoms, an aryl radical having from 6 to 50 carbon atoms, and an alkylaryl radical having from 7 to 50 carbon atoms.

3. The process as claimed in claim 1, in which $R^1$ and $R^3$ are each an organic radical which comprises between 2 and 600 alkoxy groups 4. The process of claim 1 in which $R^1$ and $R^3$ each comprise an amino group.

5. The process of claim 1 in which $R^1$ and $R^3$ each correspond to the formula 5

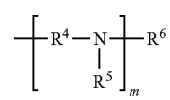
(5)

in which $R^4$ is a divalent hydrocarbon group having from 1 to 50 carbon atoms and $R^5$ and $R^6$ may each be hydrogen or a monovalent hydrocarbon group having from 1 to 50 carbon atoms, where each of $R^4$, $R^5$ and $R^6$ comprise from 1 to 200 alkoxy groups, and m is from 1 to 10.

6. The process of claim 1 in which the amine of the formula (1) is a polyamine of the formula 11

(11)

and in which $R^7$ is an n-valent organic radical having from 2 to 400 carbon atoms, $R^8$ is hydrogen or an organic radical having from 1 to 400 carbon atoms, and n is an integer from 2 to 20.

7. The process of claim 1 in which the process is conducted at a reaction temperature of from 50 to 250° C.

8. The process of claim 1 in which the process is conducted at a pressure of from 1 to 300 bar.

* * * * *